United States Patent [19]

Lippert et al.

[11] Patent Number: 4,861,652

[45] Date of Patent: Aug. 29, 1989

[54] DIAPER ARTICLE WITH ELASTICIZED WAIST PANEL

[75] Inventors: Mary E. Lippert, Outagamie County; Kenneth M. Enloe, Winnebago County; Debra J. Koch, Winnebago County; Thomas H. Roessler, Winnebago County; Patrick A. Pazdernik, Winnebago County, all of Wis.

[73] Assignee: Kimberly-Clark Corporation, Neenah, Wis.

[21] Appl. No.: 108,515

[22] Filed: Oct. 13, 1987

[51] Int. Cl.[4] .................... B05D 5/00; A61F 13/18; B32B 31/08
[52] U.S. Cl. .................................. 428/284; 428/913; 428/286; 428/152; 604/385.1; 604/383; 156/164; 156/163
[58] Field of Search .................... 604/385.1, 383; 428/913, 284; 156/164, 163

[56] References Cited

U.S. PATENT DOCUMENTS

| | | | |
|---|---|---|---|
| 3,402,715 | 9/1968 | Liloia et al. | 128/287 |
| 3,721,242 | 3/1973 | Krusko | 128/287 |
| 3,766,922 | 10/1973 | Krusko | 128/284 |
| 3,951,150 | 4/1976 | Schaar | 128/287 |
| 4,036,233 | 7/1977 | Kozak | 128/287 |
| 4,041,949 | 8/1977 | Kozak | 128/287 |
| 4,047,530 | 9/1977 | Karami | 128/287 |
| 4,094,319 | 6/1978 | Joa | 128/284 |
| 4,285,747 | 8/1981 | Rega | 156/164 |
| 4,381,781 | 5/1983 | Sciaraffa et al. | 604/372 |
| 4,388,075 | 6/1983 | Mesek et al. | 428/913 |
| 4,427,408 | 1/1984 | Karami et al. | 604/393 |
| 4,515,595 | 5/1985 | Kievit | 604/385 |
| 4,552,795 | 11/1985 | Hansen et al. | 156/163 |
| 4,585,449 | 4/1986 | Karami | 604/378 |
| 4,663,220 | 5/1987 | Wisneski et al. | 428/221 |
| 4,685,916 | 8/1987 | Enloe | 604/385 |
| 4,720,415 | 1/1988 | Vander Wielen et al. | 428/152 |
| 4,762,521 | 8/1988 | Roessler et al. | 604/385.1 |

FOREIGN PATENT DOCUMENTS

| | | | |
|---|---|---|---|
| 219969A1 | 4/1987 | European Pat. Off. | |
| 2023431 | 1/1980 | United Kingdom | 604/385.1 |
| 2130491 | 6/1984 | United Kingdom | 604/385.1 |

Primary Examiner—George F. Lesmes
Assistant Examiner—Nizar M. Ibrahim
Attorney, Agent, or Firm—Paul Yee

[57] ABSTRACT

The present invention provides a distinctive absorbent article which includes a backsheet layer which delimits at least one waistband portion of the article. A substantially liquid-permeable topsheet layer is located in facing relation with an inner surface of the backsheet layer, and an absorbent body is located between the topsheet layer and the backsheet layer. An elastic member, which is connected to the waistband portion, is composed of an elastomeric, nonwoven fibrous web material, and is constructed and arranged to shirr the waistband portion.

39 Claims, 9 Drawing Sheets

DIAPER ARTICLE WITH ELASTICIZED WAIST PANEL

FIELD OF THE INVENTION

The present invention relates to an absorbent article having an elasticized waistband. More particularly, the present invention relates to a disposable absorbent garment, such as a disposable diaper, having a centrally located elasticized panel positioned along the edge of the front and/or rear waistband portions of the garment.

BACKGROUND OF THE INVENTION

Conventional absorbent articles, such as disposable diapers, have employed elastic members secured to the waistband portions of the article. For example, see U.S. Pat. No. 3,951,150 issued Apr. 20, 1976 to C. Schaar and U.S. Pat. No. 4,427,408 issued Jan. 24, 1984 to H. Karami, et al.

Since the garment material is typically nonstretchable and since the waist elastic must be aligned along the side-to-side, crossdirection of the garment, the integration of the elastic member into the garment waistband has been difficult. One technique for addressing this difficulty is described in U.S. Pat. No. 4,285,747 issued Aug. 25, 1981 to J. Rega. In this technique, a web is foreshortened in the transverse direction and the end portions of an unstretched elastic member are adhered transverse of the web. The foreshortened web is then returned to its original dimension and the stretched central portion of the elastic member is adhered to the web.

Other techniques have employed notched or slits formed through the garment waistband material. For example, see U.S. Pat. No. 4,381,781 issued May 3, 1983 to M. Sciaraffa, et al. and U.S. Pat. No. 4,036,233 issued July 19, 1977 to T. Kozak. Unstretched elastic members can then be attached to the garment waistbands. The notches or slits allow the garment waistband material to expand when tension is applied to stretch the elastic member.

In addition, specific diaper designs have been configured to allow some escape of vapors past a garment waistband through passages formed between the outer backsheet and the inner liner of the garment. For example, see U.S. Pat. No. 4,515,595 issued May 7, 1985 to D. Kievit, et al. and European Patent Application EP No. 0 219 969 A1 published Apr. 29, 1987 with the inventors listed as J. Daugan, et al. Daugan, et al. describe a disposable diaper having a waistband which is gathered by an elastic strip composed of an open-cell polyurethane foam. Such elastic foam strips may, however, excessively discolor or deteriorate during use.

Conventional elasticized waistband designs, however, have not been able to provide a desired combination of fit, comfort, containment and appearance. Garment waistband sections typically have been soft and flexible to reduce irritation of the wearer's skin. When such flexible waistbands are elasticized, however, they can excessively tuck inwardly or outwardly and allow the formation of gaps around the waist and leg areas of the garment. Such gaps can increase the potential for excessive leakage. The garment waistband may be stiffened to address this problem, but such stiffening can create increased irritation and red marking of the wearer's skin. For example, the corrugated waistband design described in U.S. Pat. No. 4,515,595 to Kievit, et al. may suitably stiffen the waistband, but also can provide a stiff, harsh waistband edge that can irritate the wearer. Conventional garment waistband designs have also provided insufficient breathability past the waistband and have presented an undesired plastic-like appearance. As a result, further improvements to the design of elasticized waistbands have been desired.

BRIEF DESCRIPTION OF THE INVENTION

The present invention provides an absorbent article which has a distinctive elasticized waistband portion. Generally stated, the absorbent article includes a backsheet layer which delimits at least one waistband portion of the article. A substantially liquid permeable topsheet layer is located in facing relation with an inner surface of the backsheet layer, and an absorbent body is located between the topsheet layer and the backsheet layer. An elastic member, which connects to the waistband portion, is composed of an elastomeric, nonwoven fibrous web material and is arranged to shirr the waistband portion of the article. Alternatively, the elastic member may be connected to an inner or outer surface of the topsheet layer.

The article of the present invention provides a pleasing, clothlike appearance at the garment waistband, and can provide improved fit and containment of liquids. In particular aspects of the invention, the elasticized waistband can provide increased resistance to rollover while reducing irritation and red marking of the wearer's skin. In further aspects of the invention, the garment waistband can provide increased breathability at the wearer's waist and can reduce sagging and gapping at the waist and leg regions of the garment. The reduced gapping helps to improve the containment of liquids and other viscous fluids within the garment.

BRIEF DESCRIPTION OF THE DRAWINGS

The present invention will be more fully understood and further advantages will become apparent when reference is made to the following detailed description of the invention and the following drawings, in which.

DETAILED DESCRIPTION OF THE INVENTION

The following detailed description will be made in the context of a disposable diaper article. It is readily apparent, however, that the present invention would also be suitable for other absorbent articles, such as infant training pants, incontinence garments and the like.

Figure 1:
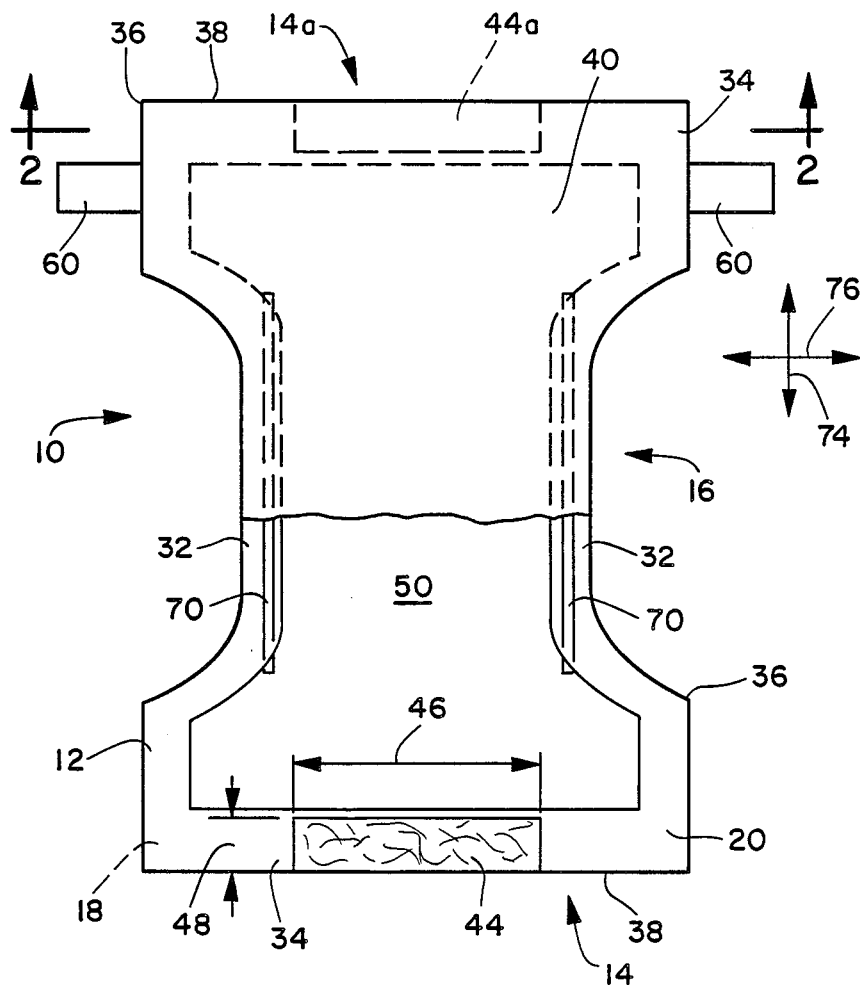
FIG. 1 shows a plan view of a representative absorbent garment of the invention in its ungathered condition.
Figure 2:
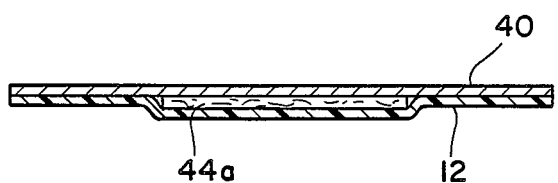
FIG. 2 representatively shows a cross-sectional view (not to scale) taken along line 2—2 of FIG. 1.

With reference to FIG. 1, an absorbent article, such as diaper 10, includes a substantially liquid impermeable backsheet layer 12 which delimits at least one waistband portion 14a of the diaper. A substantially liquid permeable topsheet layer 40 is located in facing relation with an inner surface 20 of the backsheet layer, and an absorbent body 50 is located between the topsheet layer and the backsheet layer. An elastic member 44, which is composed of an elastomeric, nonwoven fibrous web, is connected to a selected surface of the diaper waistband, such as an inner or outer surface of the backsheet waistband portion, and is arranged to shirr at least topsheet layer 40. Alternatively, the elastic member may operably connected to an inner or outermost surface of the topsheet layer. For example, in one aspect of the invention, the elastic member may be laminated between the backsheet and topsheet layers to form a gathered, composite waistband portion of the diaper. Particular configurations of the invention include an elastic member composed of an elastomeric, nonwoven fibrous material having an overall bulk thickness dimension, of at least about 0.025 inch, as measured in its untensioned, contracted state. In addition, the resultant composite waistband portion can have a buckling force value within the range of about 30–50 grams-force.

Figure 4:
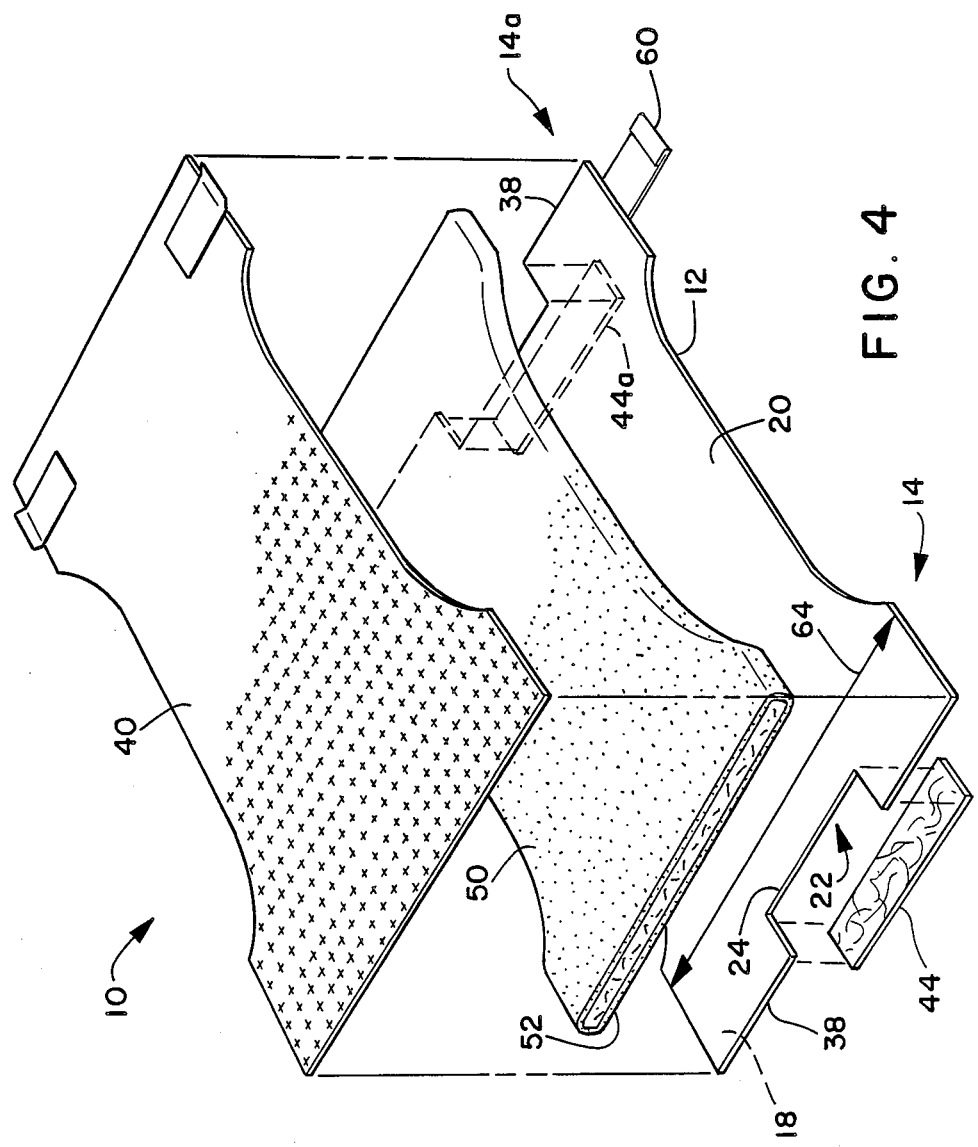
FIG. 4 representatively shows an alternative embodiment of the invention which includes a relieved section formed in the backsheet layer.

In another aspect of the invention representatively shown in FIG. 4, diaper 10 includes a backsheet layer 12 having at least one waistband portion 14, and more typically having both a front waistband portion 14 and a back waistband portion 14a. One or more of the backsheet waistband portions has a relieved, reduced-stiffness section 22 formed therein. A substantially liquid-permeable topsheet layer 40 is located in facing relation with a bodyside, inner surface 20 of the backsheet layer, and at least a portion of the topsheet spans over reduced-stiffness section 22 of the backsheet waistband portion. Absorbent body 50 is located between topsheet layer 40 and backsheet layer 12. In addition, an elastic member 44 is connected to an inner or outer surface of waistband portion 14 of backsheet 12 and spans at least partially over reduced-stiffness section 22. The elastic member is composed of an elastomeric, nonwoven fibrous material which is connected and arranged to gather and shirr at least a portion of the topsheet layer.

While the present description relates to an absorbent article which has an improved elasticized waistband positioned at a single, front waistband region of the article, it is contemplated that a similar elasticized waistband can be positioned at a rear waistband region of the article. Accordingly, it will be readily apparent that any portion of the description which pertains to one elasticized waistband region can pertain equally to any other elasticized waistband regions of the article.

In the illustrated embodiments, backsheet 12 and topsheet 40 are essentially coterminous and extend out past the edges of absorbent body 50 to form end margins 34 and side margins 32. Diaper 10 generally defines and delimits diaper waistband portions 14 and 14a at each longitudinal end thereof and defines an intermediate section 16 which interconnects the waistband portions. The illustrated embodiments of the invention include an intermediate portion which is narrower than the waistband portions. Diaper 10 thusly forms a generally hourglass or I-shape planform with the waistband portions 14 and 14a each defining ear sections 36 which extend oppositely along the lateral cross-direction 76 of the diaper. Two ear sections at one waistband portion of the diaper include securement means for fastening the diaper on the wearer. In the shown embodiments, the securement means are operably connected to the ear sections of rear waistband portion 14a of the diaper, and comprise pressure-sensitive adhesive tape tabs 60. It is readily apparent, however, that various other securement means, such as hooks, snaps, cohesive strips and the like could also be employed. The illustrated embodiment further includes leg elastic members 70 which are attached to each of the garment side margins 32 and configured to gather and shirr the legband portions of the garment to form seals or gaskets about the legs of the wearer. In addition, diaper 10 can include waist elastic members 44 and 44a secured to one or more of end margins 34 to gather and shirr the waistbands of the diaper.

The various components of diaper 10 are assembled together employing conventional techniques. For example, the components may be attached to one another employing thermal or sonic bonds, or mechanical fasteners, such as snaps or clips. Alternatively, the components can be attached with adhesives, such as hotmelt pressure-sensitive adhesives. The adhesives can be applied by conventional techniques, such as by spraying droplets or filaments of the adhesive. In the shown embodiment, the components are assembled by employing a plurality of generally parallel lines of hotmelt pressure-sensitive adhesive aligned along the length dimension 74 of the diaper. The adhesive lines are configured and arranged to bond the backsheet and topsheet to the absorbent body, and bond the marginal edges of the topsheet to the corresponding, adjacent marginal edges of the backsheet.

In a particular embodiment of the invention, diaper 10 includes a backsheet composed of a liquid-impermeable, substantially inelastic material, such as a polymer film. For example, backsheet 12 can be composed of a polyolefin film, such as polyethylene or polypropylene. In another embodiment of the inventon, backsheet 12 can be composed of a liquid-impermeable but vapor-permeable material, such as a "breathable", microporous polyethylene film.

The polymer film typically has a thickness within the range of about 0.0005–0.002 inches (about 0.0013–0.0051 cm). Preferably, however, the polymer film has a thickness within the range of about 0.00075–0.0015 inches (about 0.0019–0.0038 cm), and more preferably has a thickness within the range of about 0.001–0.00125 inches (about 0.00254–0.0032 cm) to provide greater softness and a lower resistance to gathering and shirring.

Alternatively, backsheet 12 may comprise a nonwoven, fibrous web which has been suitably constructed and arranged to be substantially liquid impermeable. The nonwoven fibrous web may also be constructed to be liquid-impermeable but vapor-permeable. For example, the nonwoven fibrous web may be treated with a selected polymer coating or film to impart a desired degree of liquid impermeability and vapor permeability. Typically, the nonwoven fibrous web has a basis weight within the range of about 0.9–2.5 oz/yd$^2$, and preferably has a basis weight within the range of about 1.3–1.7 oz/yd$^2$ to provide improved comfort.

Topsheet 40 is typically composed of a liquid-permeable, elastic or inelastic, and substantially hydrophobic material, such as a spunbonded web composed of synthetic polymer filaments. Alternatively, topsheet 40 may comprise a meltblown web or a bonded-carded-web composed of synthetic polymer filaments. Suitable synthetic polymers include, for example, polyethylene, polypropylene and polyesters. The topsheet has a pore size that readily allows the passage therethrough of liquids, such as urine and other body exudates. Optionally, the topsheet can be treated with surfactants to selectively adjust its degree of wettability, and can also be selectively embossed or perforated with discrete slits or holes extending therethrough. Suitable topsheet materials have a thickness within the range of about 0.005–0.025 in (about 0.013–0.064 cm) and preferably have a thickness of within the range of about 0.010–0.020 in (about 0.0254–0.051 cm) to provide improved effectiveness. For the purposes of the present invention the thickness dimension of the topsheet material can be determined by employing an Ames Bulk Test (ASTM D-1777) performed at a restraining pressure of 0.2 psi (1.38 kPa).

Absorbent body 50 typically comprises a pad composed of airlaid, cellulosic fibers commonly referred to as wood pulp fluff. Conventional pads can have a density ranging from about 0.05–0.20 g/cc, and are sufficiently flexible to readily conform to the body of the wearer. Absorbent body 50 may alternatively comprise a coform material composed of a mixture of cellulosic fibers and synthetic polymer fibers. For example, the coform material may comprise an airlaid blend of cellulosic fibers and meltblown polyolefin fibers, such as polyethylene and polypropylene fibers. The absorbent body may also include an effective amount of an inorganic or organic high-absorbency material to enhance the absorptive capacity of the absorbent body. For example, absorbent body 50 can include 5–95 wt % high-absorbency material, and preferably includes about 10–30 wt % of the high-absorbency material to provide more effective peformance. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, and isobutylene maleic anhydride copolymers, and mixtures thereof. The hydrogel polymers are preferably lightly cross-linked to render the materials substantially water-insoluble. Cross-linking may, for example, be by irradiation or by covalent, ionic, Van der Waals, or hydrogen bonding. Suitable materials are available from various commercial vendors, such as Dow Chemical Company, Celanese Corporation, Allied-Colloid, and Stockhausen. Typically, the high-absorbency material is capable of absorbing at least about 15 times its weight in water, and preferably is capable of absorbing at least about 25–50 times its weight in water.

The high-absorbency material can be distributed or otherwise incorporated into absorbent body 50 employing various techniques. For example, the high-absorbency material can be substantially uniformly distributed in the mass of fibers comprising the absorbent body. The material can also be nonuniformly distributed among the fibers to form a generally continuous gradient with either an increasing or decreasing concentration of high-absorbency material, as determined by observing the concentration moving from the bodyside of absorbent body 50 to the outerside of the absorbent body. Alternatively, the highabsorbency material can comprise a discrete layer separate from the fibrous material of absorbent body 50 or can comprise a discrete layer integral with the absorbent body.

Absorbent body 50 can optionally include a tissue wrap 52 to help maintain the integrity of the airland fibrous structure. The tissue wrap typically comprises a hydrophilic cellulosic material, such as creped wadding or a high wet-strength tissue, and may extend over either or both of the outer and bodyside surfaces of the absorbent body.

While the particular embodiments shown in the Figures illustrate an absorbent body which is substantially permanently attached to the backsheet layer, it is contemplated that the absorbent body may optionally be removeably attached to the backsheet. For example, the absorbent body may comprise a removeable insert which is temporarily affixed to a reusable backsheet member.

Waist elastic member 44 is composed of an elastomeric, cloth-like, nonwoven fibrous material, such as an elastomeric stretch-bonded laminate (SBL) web or an elastomeric meltblown web. In a particular aspect of the invention, elastic members 44 are composed of an elastomeric, nonwoven fibrous web which is substantially vapor-permeable. The fibrous, nonwoven, elastomeric material employed in the waistband of the present invention provides a particularly pleasing appearance and provides a softer edge at the diaper waistband which is less likely to cut or otherwise irritate the skin of the wearer. Where the diaper waistband section is constructed to be vapor permeable, the diaper garment also can provide greater comfort.

Examples of suitable meltblown elastomeric fibrous webs for forming waist elastic member 44 are described in U.S. Pat. No. 4,663,220 issued issued May 5, 1987 to T. Wisneski, et al., which is incorporated herein by reference. Examples of composite fabrics comprising at least one layer of nonwoven textile fabric secured to a fibrous elastic layer are described in European Patent Application EP No. 0 110 010 published on Apr. 8, 1987 with the inventors listed as J. Taylor, et al which is incorporated herein by reference. The composite nonwoven fabrics are commonly referred to as stretch-bonded laminates.

In yet another aspect of the invention, elastic member 44 can be composed of an elastomeric, stretchable composite web comprising individual, discrete strips of elastomeric material secured to one or more nonwoven fibrous layers. Such a composite web may, for example, comprise an elastomeric meltblown material arranged in a selected pattern of strips and suitably sandwiched and attached between two layers of nonwoven, spunbond, fibrous material. The composite web may alternatively comprise a selected pattern of individual elastomer strips operably secured to a nonwoven fibrous layer or between two nonwoven layers. The elastomer strips may, for example, be composed of a thermoplastic, melt extrudable material. Examples of suitable elastomer materials include polyether-polyamide block copolymers, polyurethanes, synthetic linear A-B-A and A-B block copolymers, chlorinated rubber/EVA (ethylene-vinyl acetate) blends, EPDM (ethylene-propylene diene monomer) rubbers, EPM (ethylene-propylene monomer) rubbers, blends of EPDM/EPM/EVA, and the like.

In an embodiment of the invention representatively shown in FIG. 1, the absorbent article includes a backsheet layer 12 which defines at least one backsheet waistband portion, and more typically defines and delimits a front waistband portion 14 and a rear waistband portion 14a. Elastic member 44 is sandwiched and suitably attached between backsheet layer 12 and topsheet layer 40, and is arranged to extend to the terminal, longitudinal waistband edge 38. Ordinarily, the longitudinal terminal edge of backsheet 12 can be harsh and may irritate the skin of the wearer. To improve the comfort of the diaper and reduce excessive irritation, waist electric member 44 is configured to have a selected minimum thickness dimension which operably spaces backsheet 12 away from topsheet 40 by an amount which is sufficient to effectively reduce irritation. In a particular aspect of the invention, elastic member 44, as measured in its untensioned contracted state, has an overall bulk thickness dimension of at least about 0.025 in (about 0.064 cm) and preferably has a thickness of at least about 0.050 in (about 0.127 cm) to provide improved effectiveness.

Accordingly, the elastic member can operably space the terminal, longitudinal edge of the backsheet from the corresponding edge of the topsheet by a minimum distance which approximately corresponds to the thickness of the elastic member. The separation cooperates with the resilience of the material comprising elastic member 44 and with the topsheet to reduce and cushion any contact between the backsheet and the wearer's skin. In a particular aspect of the invention, the composite elasticized waistband, when measured in its untensioned gathered condition, has a total bulk thickness of at least about 0.050 in (about 0.127 cm), and preferably has a bulk thickness of at least about 0.075 in (about 0.19 cm) to provide improved effectiveness. A suitable technique for determining the thickness of the composite waistband is an Ames Bulk Test (ASTM D-1777) performed while employing a restraining pressure of 0.2 psi (1.38 kPa).

Figure 3:
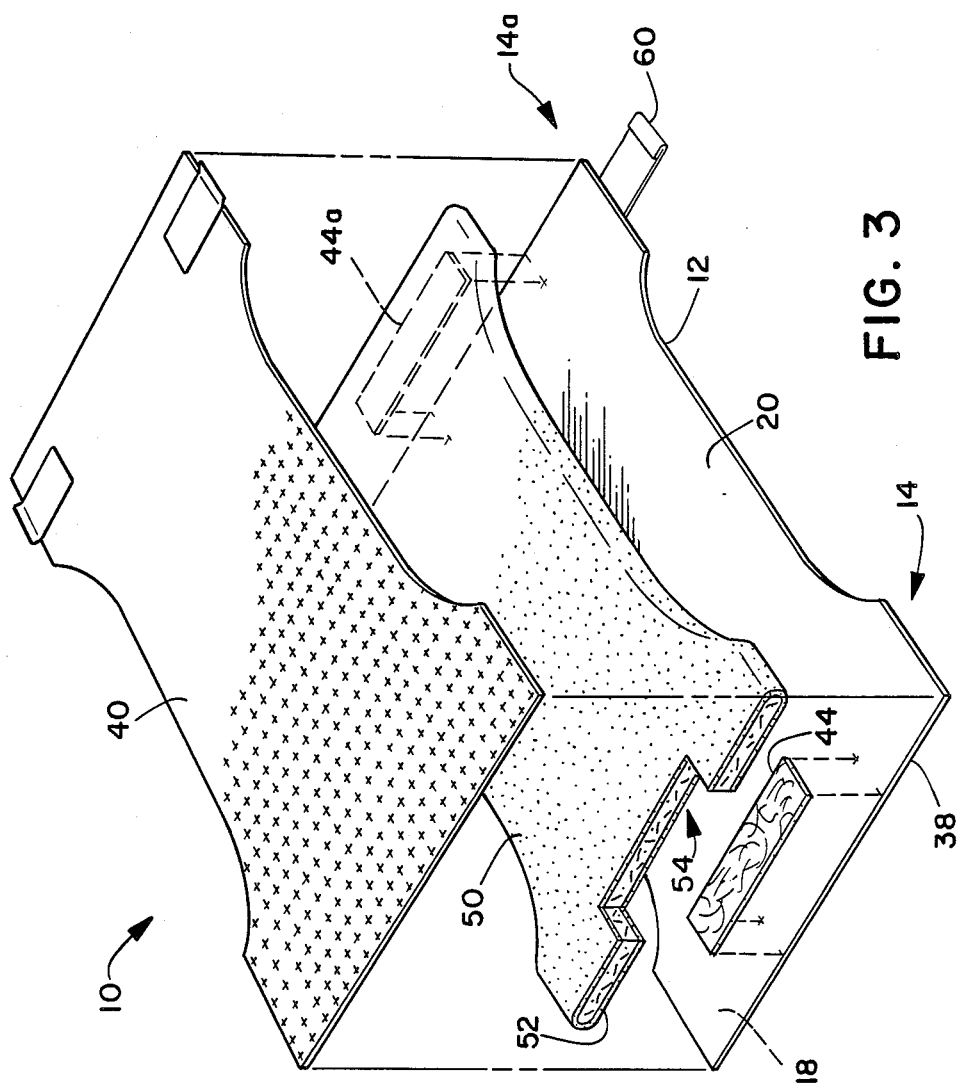
FIG. 3 representatively shows another embodiment of the invention.

To further help to reduce waistband rollover, another aspect of the invention includes an absorbent body having a notch recess 54 formed into one or more longitudinal end edges of the absorbent, as representatively shown in FIG. 3. Elastic member 44 is located adjacent to or within the open, "mouth" portion of the recess and spans at least partially across the open section of the recess. With this arrangement, the absence of absorbent material from the notch region reduces the resistance of the diaper structure therein to the gathering force exerted by the elastic member, and allows the use of an elastic material having a lower and gentler elastic modulus. In addition, the presence of the absorbent material at the lateral side edges of the recess can advantageously support the diaper waistband and inhibit any tendency of the elasticized portion of waistband to roll over toward or away from the body of the wearer.

While the illustrated notch recess 54 is generally rectilinear in shape, it is readily apparent that the recess may alternatively have an arcuate or curvilinear shape configured such that at least an effective portion of the terminal longitudinal edge of absorbent body 50 recedes away from the adjacent, corresponding edge of the backsheet. A more detailed description of the notched absorbent pad can be found in U.S. Pat. No. 4,685,916 issued Aug. 11, 1987 to K. Enloe, which is hereby incorporated by reference, to the extent that it is consistent with the present specification.

Alternative arrangements may also be employed to improve the gatherability of the waistband structure and enhance the appearance of the diaper. For example, the absorbent pad may be thinner or tapered at the pad edges located at the diaper waistband. The tapered edges may or may not include notched areas formed therein.

In the embodiment of the invention illustrated in FIG. 4, backsheet layer 12 defines at least one backsheet waistband portion, and more typically defines and delimits a front waistband portion 14 and a rear waistband portion 14a. At least one and preferably both of the waistband portions have a reduced-stiffness sections 22 formed therein. The material of the reduced-stiffness section is suitably altered or otherwise modified to provide a discrete region, at least a portion of which has a stiffness value which is less than the stiffness value of the other remaining sections of the backsheet material. Each reduced-stiffness section may, for example, comprise a portion of backsheet 12 which has a notched recess, apertures or a selected pattern of embossments formed therein. FIG. 4 representatively shows a configuration in which a relieved notch section 24 having generally rectilinear edge borders is formed into an end margin 34 of diaper 10. Alternatively, the notch recess may have curvilinear or irregular edge borders.

Figure 5:
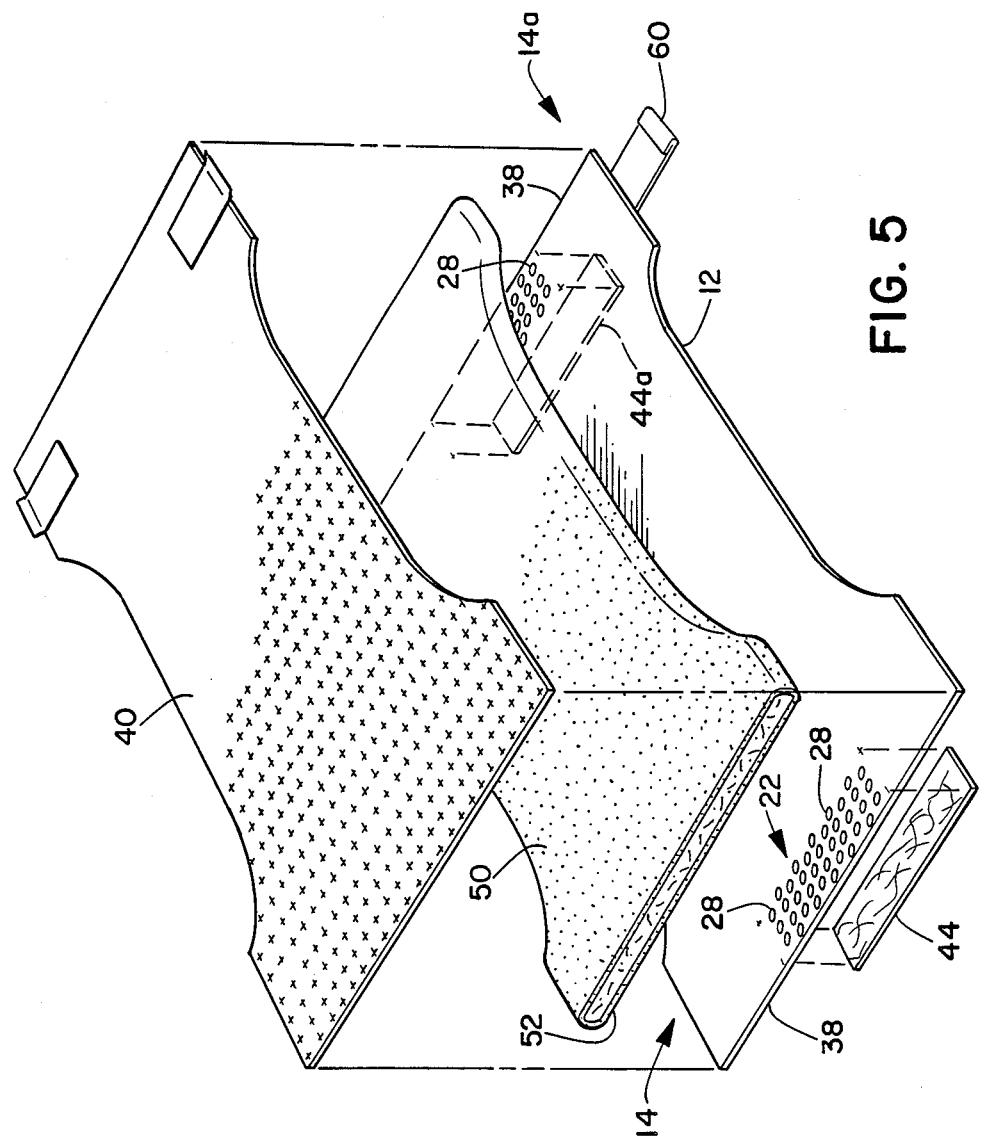
FIG. 5 representatively shows an embodiment of the invention in which the relieved section of the garment backsheet has apertures or embossments formed therein.
Figure 6:
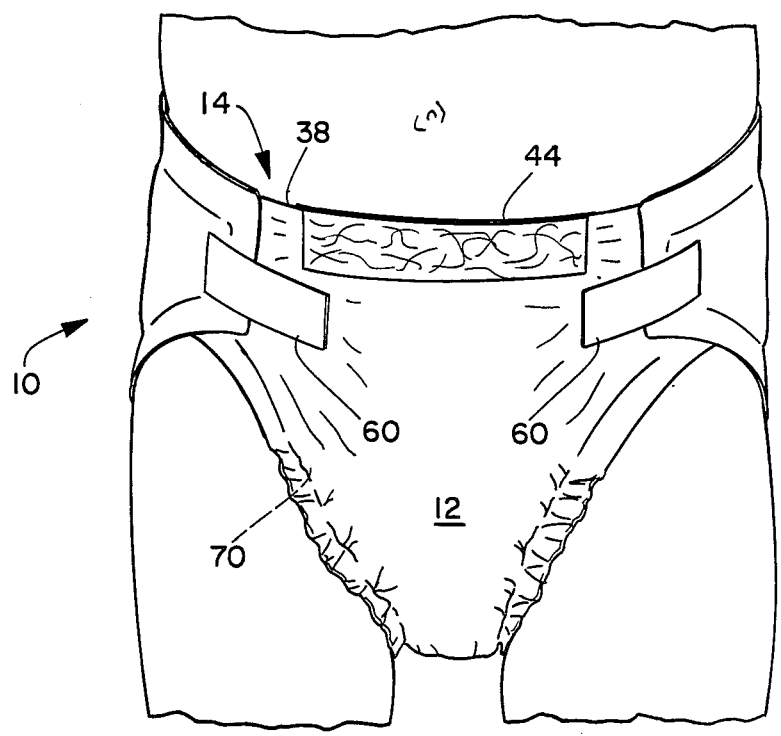
FIG. 6 representatively shows an absorbent article of the invention as worn by an infant.

As representatively shown in FIG. 5, the relieved, reducedstiffness section 22 can comprise a portion of end margin 34 which has a plurality of embossments or apertures 28 formed therethrough. The apertures may comprise slits, perforations or holes arranged in a regular or irregular pattern, as desired. Similarly, the embossments may have a regular or irregular shape and may be arranged in a regular or irregular pattern, as desired.

The reduced-stiffness section formed in the end margins of backsheet 12 can advantageously soften the backsheet material and render it more susceptible to gathering and shirring under the influence of the waist elastic member 44. The resultant elasticized waistband can then provide greater comfort and be less likely to irritate the skin of the wearer.

In a particular aspect of the invention, reduced-stiffness secton 22 extends across at least about 20% of the cross-directional width 64 of waistband 14, and preferably extends across about 35–55% of the waistband width. In addition, reduced-stiffness section 22 extends at least about 0.5 cm, preferably extends at least about 1 cm, and more preferably extends about 1–4 cm into backsheet 12, as measured from the laterally extending edge 38 of the diaper waistband. The size of the reduced-stiffness section can advantageously contribute to the improved softness and comfort of the garment. In a preferred arrangement, reduced-stiffness secton 22 is substantially centralized at the medial portion of diaper 10 along the edge of end margin 34.

With reference to FIG. 4, waist electric member 44 is connected to an outer surface 18 of backsheet 12, and spans completely over reduced-stiffness section 22 of the backsheet waistband. Alternatively, elastic member 44 may span only partially over the reduced-stiffness section, or may be connected to the inner, bodyside surface 20 of the backsheet waistband, although these arrangements may be less aesthetic. In any case, the elastic member is suitably secured to the backsheet by conventional techniques, such as adhesives, thermal bonds, sonic bonds, stitching or the like. In addition, the elastic member is operably connected and secured to topsheet 40 to gather and shirr at least the waistband portion of the topsheet. Where backsheet material is attached against elastic member 44, the elastic member also operates to gather and shirr those portions of the backsheet. For example, where the reduced-stiffness section 22 comprises an apertured region of backsheet 12, the waist elastic member is bonded or otherwise attached to the apertured material and is arranged to gather the material. Since the apertured backsheet is in turn attached to topsheet 40, the waist elastic member also gathers and shirrs the topsheet material.

To operably shirr the diaper waistband, elastic member 44 is secured to backsheet 12 while the elastic member is preferably but not necessarily in an elongated, contractible condition. For example, elastic member 44 can be mechanically held tensioned in a stretched configuration during the process of securing the elastic member to backsheet 12. When the tension is released, the elastic member can then relax and contract to gather the diaper waistband. Alternatively, elastic member 44 can comprise an oriented, elastomeric material which, upon exposure to a suitable external stimulus, can be activated to cause the elastic member to shrink from its oriented length to a shorter, contracted length. For example, elastic member 44 may comprise a thermally activatable material which contracts upon exposure to heat. Such material can be secured to backsheet 12 and topsheet 40 while in an untensioned state, and then later activated to contract to a shorter, elasticized state. Upon the contraction, the elastic member can operably gather and shirr the diaper waistband.

To improve the fit and appearance of the waistband section, elastic member 44 is configured to have a length dimension 46 which extends over at least about 20% of the cross-directional width of the particular absorbent article. Preferably the elastic member extends across at least 40% and more preferably extends across at least about 50% of the article's cross-directional width to provide improved performance. More particularly, for the illustrated diaper article of the invention, elastic member 44 has a length dimension 46 of at least about 2.0 cm. Preferably, the length of the elastic member is within the range of about 2.5-33 cm, and more preferably, is within the range of about 10-20 cm to provide improved performance. In addition, elastic member 44 is configured to have a width dimension 48 of at least about 1.0 cm. Preferably, the width of the elastic member is within the range of about 2-7.5 cm and more preferably, is within the range of about 2.5-4 cm to provide improved effectiveness. As a result, elastic member 44 covers an area within the range of about 2.5-262 sq. cm, and preferably covers an area within the range of about 25-80 sq. cm. The increased area over which the elastic force of elastic member 44 is applied advantageously distributes the force and reduces pressure exerted against the body of the wearer. The lower pressure can reduce the potential for irritation and red marking the wearer's skin. For the purposes of the present invention, the above-described dimensions for elastic member 44 are determined with respect to an assembled article in its free-standing, gathered condition wherein the elastic member has contracted to shirr the elasticized portions of the article.

In one aspect of the invention, the elasticized waistband of the diaper is configured to provide increased resistance against waistband rollover without providing an excessively harsh edge that could irritate the wearer's skin. End margins 34 of diaper 10 are typically made soft and flexible to avoid skin irritation or abrasion and to facilitate the desired shirring by waist elastic 44. The flexibility of end margin 34, however, may allow the elasticized portion of the end margin to roll over and tuck inwardly or outwardly relative to the body of the wearer during use. The rolling over of the diaper waistband may then allow the diaper to sag and create gaps around the waist and legs. Such sagging and gapping can then contribute to increased leakage of fluids from the diaper. To reduce the likelihood of waistband rollover, the diaper waistband section, which is composed of the laminated assembly of topsheet 40, elastic member 44, and relieved section 22 of the backsheet, should have a minimum stiffness value. The stiffness of the diaper waistband, however, should not be so great as to excessively irritate the wearer's skin.

The composite stiffness of the diaper waistband is selected to cooperate with the relatively large area extent of waist elastic 44 to provide an advantageous combination of softness, comfort and resistance to waistband rollover. A parameter for characterizing the softness and flexibility of the composite diaper waistband is a buckling force value. The waistband of the present invention exhibits a buckling force within the range of about 30-50 grams-force, and preferably exhibits a buckling force within the range of about 35-45 grams-force to provide improved effectiveness.

A suitable technique for determining the buckling force value involves mounting a test sample in a sample holder, applying a compressive force against an edge of the sample and along the plane generally defined by the sample, and then measuring the force required to displace the edge of the sample by a standard distance. More particularly, the buckling force can be determined by employing the following Buckling Test The Buckling Test employs a force measurement gauge, such as a Chatillon Gram Gauge DFG-2 manufactured by John Chatillon & Sons, Inc. of Kew Gardens Road, Kew Gardens, New York with a 0.5 inch diameter, flat, circular foot attachment; a "COMBI" Kayeness Tester or similar apparatus having a speed adjustable moving platform and mounts for the force gauge; a compressometer, such as a Standard Model Compressometer manufactured by Frazier Precision Instrument Co. of Gaithersburg, Md.; and a specialized test sample holder. Testing is performed in a standard condition atmosphere at a temperature of 23° C.±1° C. and a relative humidity of 50%±2%.

A test sample, taken from the waistband of the article being tested, measures 2 inches long and 1 inch wide with one of the 2 inch long sides corresponding to the exposed, "free" edge 38 of the waistband. This "free" edge will correspond to the "leading" edge of the test sample. The effective thickness of the test sample is measured with the compressometer at a pressure of 0.2 psi employing a 1 inch diameter foot attachment. The sample is then firmly mounted in the sample holder.

Figure 8:
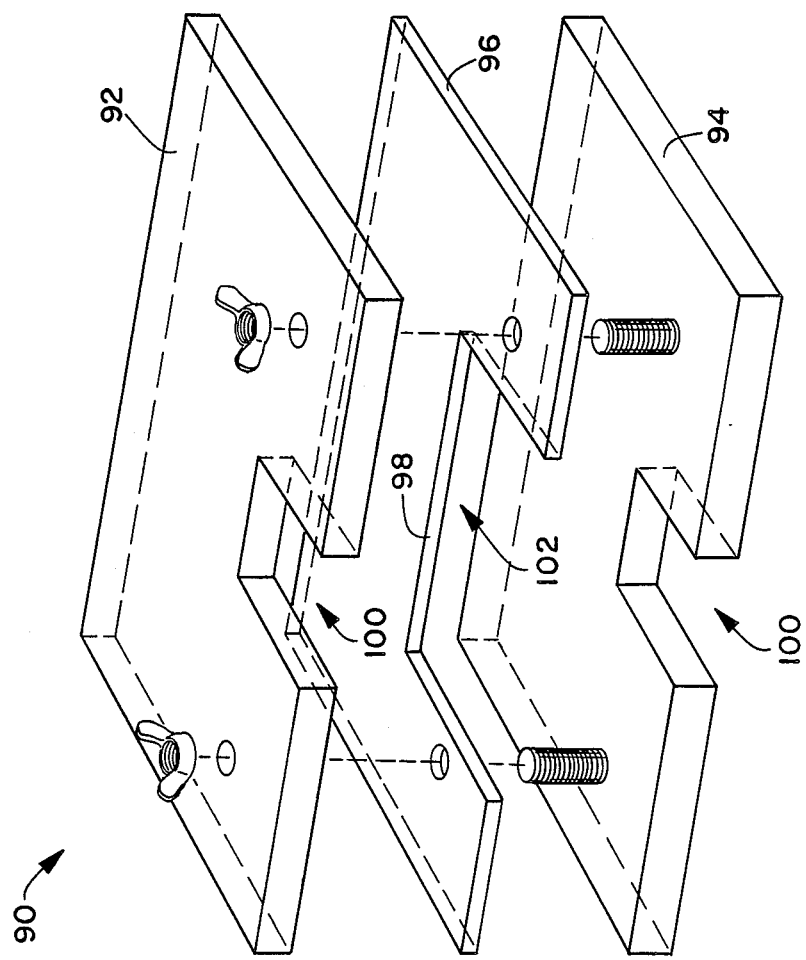
FIGS. 8, 8A, 8B, 8C, 8D and 8E representatively shows a sample holder employed to test the properties of the waistband structure of the invention.
Figure 8A:
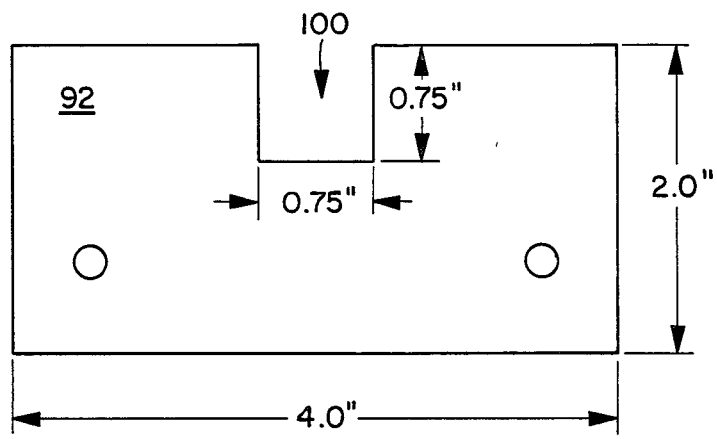
Figure 8B:
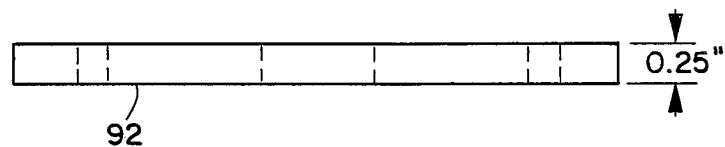
Figure 8C:
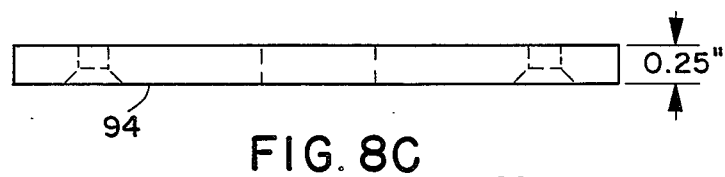
Figure 8D:
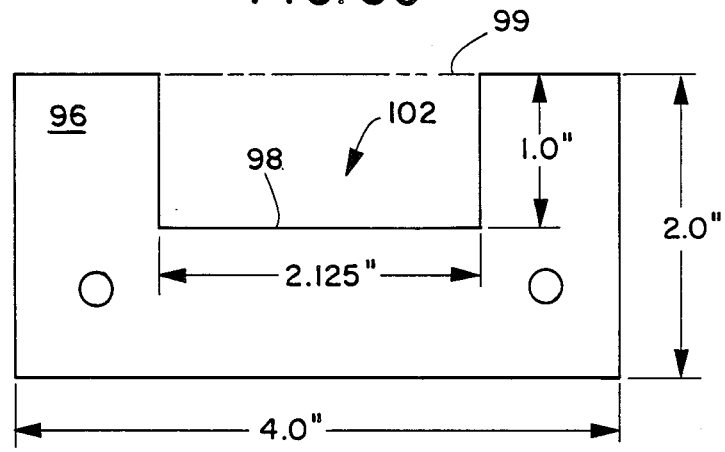
Figure 8E:

As illustrated in FIG. 8-8E, the sample holder 90 includes a top plate 92, a bottom plate 94, and a spacer 96 secured and mounted between the top and bottom plates with suitable fasteners, such as screws or bolts and wingnuts. A correctly sized spacer has a thickness which is 0.07-0.09 inch greater than the effective thickness of the test sample. In addition, the spacer has a notch 102 formed therein. The notch is sized to accommodate the sample, and is configured such that the "leading" edge 99 of the test sample does not extend past the notched end of the sample holder when the opposed edge of the test sample is butted against the inner edge 98 of the spacer. More particularly the notch in the spacer measured 2.125 inches long and 1 inch wide. Similarly, each of the top and bottom plates has a notch 100 formed therein, but these notches are generally square in shape, measuring about 0.75 inch on each side. A suitable material for making the component parts of the sample holder is plexiglass.

Figure 9:
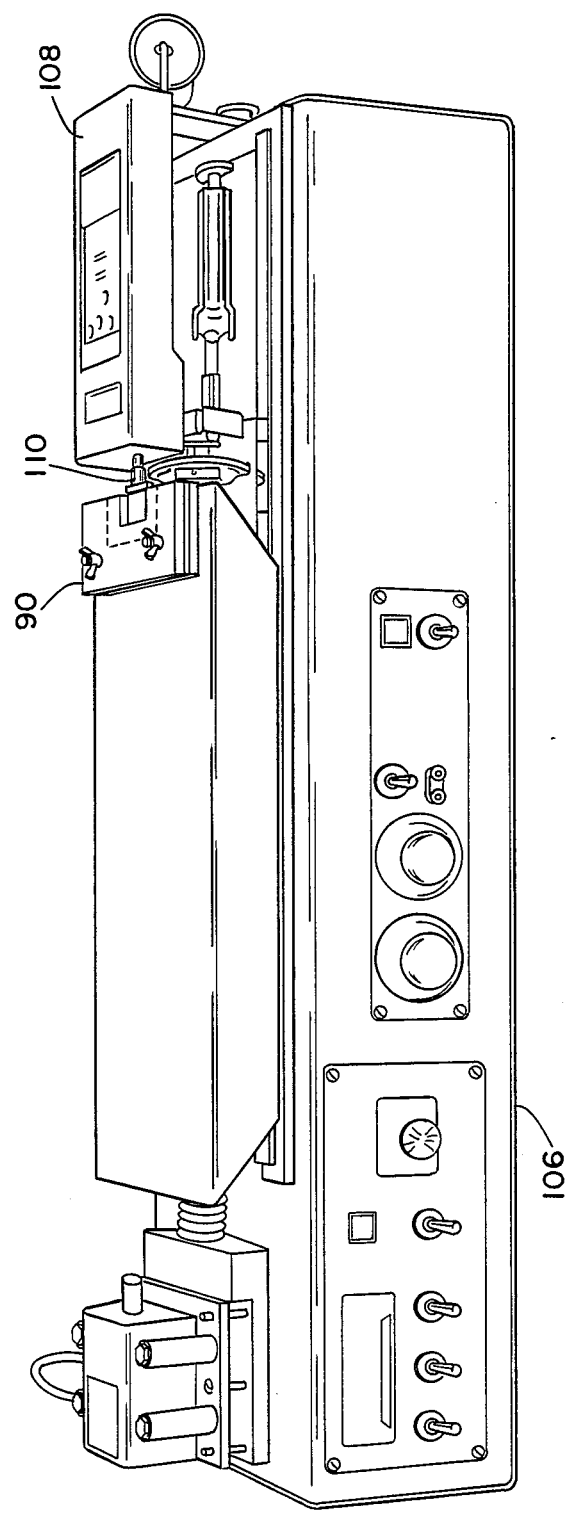
FIG. 9 representatively shows an apparatus set up to test the buckling force value of a diaper sample.

The Chatillon Gauge switches are set on "kg", "Normal" and "Compression", and as representatively shown in FIG. 9, gauge 108 is mounted onto a non-moveable portion of the Kayeness Tester 106 with the probe 110 of the gauge aligned directly over and substantially parallel to the center shaft of the Kayeness Tester. The sample holder with the test sample held therein is secured to the moveable platform employing double-sided adhesive tape, and is aligned such that the leading edge of the test sample is centered and perpendicular to the probe of Chatillon Gauge 108. Prior to making a measurement, the speed for the moveable platform of the Kayeness Tester is adjusted to 6.0±0.1 in/min and the leading edge of the test sample is positioned immediately adjacent to the foot on the Chatillon Gauge. The platform of the Kayeness Tester is advanced toward the Chatillon Gauge for a distance of 0.25±0.01 inch and then stopped. The buckling force measurement is read from the digital readout of the Chatillon Gauge, and is recorded to the nearest gram.

In another aspect of the invention, elastic member 44 is composed of a substantially vapor-permeable material to provide breathability through the thickness dimension of diaper 10 along a direction which is generally perpendicular to the plane approximately defined by the diaper waistband. Such a configuration of the invention includes a backsheet 12 which is rendered vapor-permeable by a suitable technique, such as aperturing, slitting, perforating or the like. Alternatively, backsheet 12 can be constructed from a microporous, "breathable" polymer film. Backsheet 12 can then cooperate with liquid permeable topsheet 40 and vapor-permeable elastic member 44 to provide a breathable waistband section. A desired degree of breathability is achieved when the effective porosity of the diaper waistband composite assembly provided a breathability, porosity value of at least about 3 cfm/sq. ft. Preferably, the breathability value of the waistband composite is at least about 5 cfm/sq. ft., and more preferably, is at least about 10 cfm/sq. ft. to provide improved effectiveness.

A suitable technique for determining the porosity value is the following Porosity Test, which employs a Frazier Air-Permeability Tester, manufactured by Frazier Precision Instrument Co. of Silver Springs, Md., or its equivalent. For the purposes of the present Porosity Test, the Frazier instrument is configured with its one-inch diameter top attachment orifice, and a sample is cut from the waistband of the article being tested. The test sample has a length of 2 inches and a width of 1.0-1.25 inches. A two-sided, adhesive tape is placed over the one-inch attachment orifice, and the tape material is cut away along the inside diameter edge of the attachment orifice. The test sample is then placed over the attachment orifice in its relaxed state with the bodyside topsheet layer facing downward, and is adhered to the two-sided tape. The orifice should be completely and securely covered with no gaps. The test sample is then clamped in position employing the clamping device on the Frazier apparatus. The Frazier instrument has a Powerstat control, an inclined manometer and a vertical manometer. The Powerstat is adjusted until the oil column in the inclined manometer reaches the 0.5 value. At this point the pressure drop indicated by the vertical manometer should read at least 3 inches. If this pressure drop is less than 3 inches, the Frazier instrument should be configured with a smaller flow nozzle orifice in order to provide the desired 3 inch pressure drop, if possible. The procedure for changing the appropriate nozzle is described in the instructions supplied with the Frazier instrument. After the inclined manometer oil column has steadied at the proper level, the level of the oil in the vertical manometer is read and recorded. The vertical manometer reading is then converted to a flow rate in units of cubic feet of air per minute per square foot of sample by employing the calibration/conversion table supplied with the Frazier instrument. It should be noted that the Frazier instrument has a lower measurement limit of 3 cfm/sq. ft.

Figure 7:
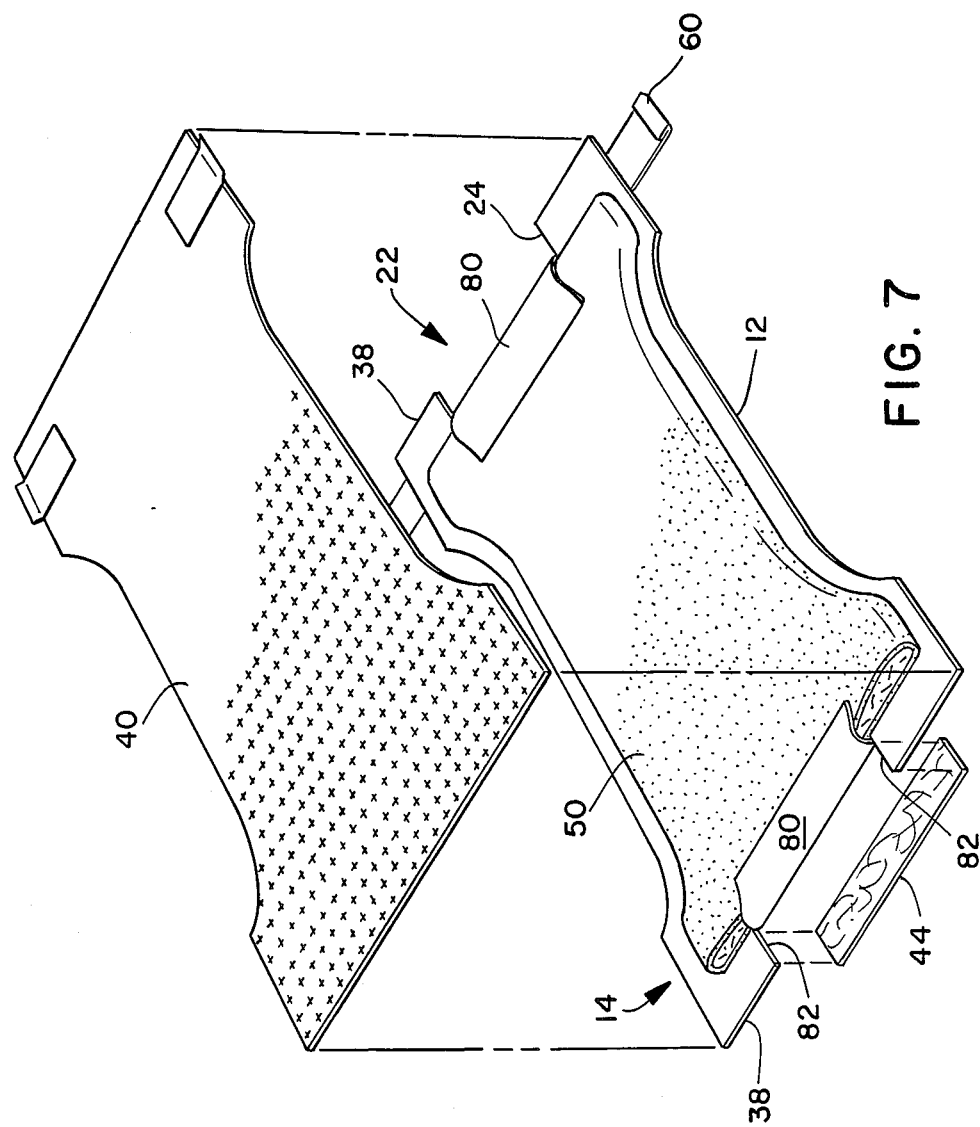
FIG. 7 representatively shows a diaper waistband in which the backsheet has been configured to provide a notched recess and a flow barrier.

In a further aspect of the invention, backsheet 12 can be distinctively configured to provide a reduced-stiffness section 22 while also providing a flow barrier which can reduce the migration of liquids past the diaper waistband. With reference to FIG. 7, reduced-stiffness section 22 is formed on backsheet 12 by cutting the backsheet to form a flap 80. Flap 80 is folded over to overlap onto the bodyside of absorbent body 50 to thereby provide a barrier against the flow of liquids. In the shown embodiment, flap 80 is formed by cutting or otherwise separating backsheet 12 along lines 82, which extend longitudinally from the edge of end margin 34 to a location proximate the adjacently located edge of absorbent body 50. Lines 82 are generally parallel to each other and are approximately symmetrically located on each side of the longitudinal centerline of diaper 10. The resultant, generally rectangular flap 80 is folded around the edge of absorbent body 50 and overlaps the inner, bodyside surface of absorbent body 50. Topsheet 40 is placed in facing relation with absorbent body 50 and overlies flap 80 to sandwich the flap between the absorbent body and the topsheet. Elastic member 44 is secured to backsheet 12 and spans completely over the reduced-stiffness section 22 defined by the generally rectangular notched recess formed into backsheet 12 by the cutting and folding over of flap 80. The portion of the elastic member which spans over the reduced-stiffness section is suitably configured and secured to topsheet 40 to gather and shirr the topsheet material when the elastic member is in its contracted condition.

In an alternative embodiment of the invention, absorbent body 50 may also include a notch recess 54 formed into either or both of its longitudinal edges, similar to the configuration illustrated in FIG. 3. With such an arrangement, separation lines 82 would extend into recess 54 and flap 80 would extend around the inner edge of the recess to overlap onto the inner surface of the absorbent body.

The following examples are given to provide a more detailed understanding of the invention. The particular materials, dimensions, amounts and other parameters are exemplary and are not intended to specifically limit the scope of the invention.

EXAMPLE 1

A disposable diaper was constructed with elasticized front and back waist panels. This absorbent article included a backsheet layer (1.28 mil polyethylene, plus titanium filler) which had a rectangular notch cut-out measuring 5.5 inch by 0.5 inch formed into each longitudinal end edge to provide a reduced-stiffness section at each waistband end of the diaper. A substantially liquid-permeable topsheet layer (0.75 oz/yd$^2$ polypropylene spundbond) was placed in facing relation with an inner surface of the backsheet layer, and an absorbent body (80 wt % airlaid cellulosic fibers, 11 wt % polyacrylate superabsorbent, and 9 wt % tissue wrap) was located between the topsheet layer and backsheet layer. The absorbent body had a bulk density of about 0.12 g/cc. An elastic member was connected to the outer surface of the backsheet waistband portion, and was composed of a three layer, elastomeric, nonwoven fibrous material. The two outer layes were composed of a polypropylene spunbond having a basis weight of about 0.4 oz/yd$^2$, and the third, middle layer was a web composed of meltblown KRATON elastomer fibers having a basis weight of approximately 95 g/m$^2$. The elastic member was affixed to the periphery of the rectangular notch and to the exposed portion of the underlying topsheet material with a sprayed hotmelt adhesive (Findley 995-372). The diaper waistband, comprising the elastic member sandwiched between the topsheet and backsheet layers, had a porosity value of 31.33 cfm/ft$^2$ and a buckling force value of 40 gm.

EXAMPLE 2

Several conventional diaper waistband structures were tested for breathability employing the above-described Porosity Test.

Sample 1 was constructed in accordance with the present invention, and had the structure described above in Example 1.

Sample 2 was a waistband which comprised a backsheet layer (1.28 mil polyethylene plus titanium filler), and a substantially liquid permeable topsheet layer (0.75 ounce/square yard polypropylene spunbond). The backsheet was positioned in facing relation to the inner surface of the topsheet and attached to the topsheet with hotmelt glue lines (Findley 694-373B, glue lines approximately 0.5" apart). An elastic member (oriented coextruded film 0.44 inches by 5.5 inches) was attached to the backsheet layer with two parallel hotmelt adhesive glue lines (Findley 191-335B) and secured in the center of the waistband portion (1.5 inches by 13 inches). The elastic member was sandwiched between the backsheet and topsheet layers. The waistband structure of Sample 2 substantially corresponded to the structure found in a commercial product marketed by Kimberly-Clark Corporation.

Sample 3 was a waistband which comprised a backsheet layer (1.38 mil polyethylene plus titanium dioxide filler), and a substantially liquid permeable topsheet layer (0.75 ounce per square yard heat bonded polypropylene). The backsheet was located facing relation to the inner surface of the topsheet and attached to the topsheet with hotmelt glue lines (polystyrene/polybutadiene base polymer with terpene resin, approximately 0.875 inches apart). An elastic member (EVA heat shrinkable film, 3.5 mil, EPDM/polypropylene santoprene, one inch by seven inch) was sandwiched between and shirred to the topsheet and backsheet with rows of ultrasonic bonds approximately 0.3 inches apart. The elastic member extended to the leading edge of the waistband. The waistband structure of Sample 3 was obtained from a commercial product distributed by Procter & Gamble Co. under its LUVS brand name.

Sample 4 was a waistband comprising a backsheet layer (1.38 mil polyethylene plus titanium dioxide filler); a substantially liquid permeable topsheet layer (0.75 ounce per square yard heat bonded polypropylene); and a waist barrier material (isotactic polyisopropylene mylar type film, 1.1 mil, 2.1 inches by 12.0 inches). The waist barrier material is sandwiched between the backsheet and the topsheet, and is attached to the topsheet with sonic bonds, and is attached to the backsheet with lines of hotmelt adhesive (polystyrene/polyisoprene base polymer with tackifier) spaced approximately 0.5 inches apart. The waistband structure of Sample 4 was obtained from a commercial product distributed by Procter & Gamble under its PAMPERS brand name.

The Porosity Test results are summarized in Table 1 below.

TABLE 1

| Diaper Waistband Porosity | |
|---|---|
| Diaper Sample | Porosity (CFM/SQ FT) |
| Sample 1 | 31.33 |
| Sample 2 | less than 3.53 |
| Sample 3 | less than 3.53 |
| Sample 4 | less than 3.53 |

EXAMPLE 3

The four diaper waistband structures described in Example 2 along with a fifth sample were tested for buckling force employing the above-described Buckling Test.

Sample 5 was constructed in accordance with the present invention, and had a structure comprising a backsheet layer (1.00 mil polyethylene plus titanium dioxide filler), and a substantially liquid permeable topsheet layer (0.75 ounce per square yard polypropylene spunbond) placed in facing relation with the inner surface of the backsheet layer. The backsheet was attached to the topsheet with a hotmelt spray adhesive (National 70-2911). An elastic member (1.125" by 6.0" tensioned) composed of an elastomeric nonwoven fibrous material (95 mil, 210 grams per square inch, composed of: 0.4 ounce per square yard polypropylene spunbond, 95 grams per square yard meltblown KRATON, and 0.4 ounce per square yard polypropylene spunbond) was attached to the backsheet layer with parallel hotmelt adhesive glue lines (Findley 191-335B) spaced approximately 0.18 inches apart and secured to the center of the waistband portion (1.5" by 13"). The elastic member was sandwiched between the backsheet and topsheet layers. Five individual specimens of Sample 5 were tested, and the average test value was recorded.

The test results are summarized in Table 2 below.

TABLE 2

| Diaper Buckling Force | |
|---|---|
| Diaper Sample | Buckling Force (Grams) |
| Sample 1 | 40 |
| Sample 2 | 23 |
| Sample 3 | 59 |
| Sample 4 | 23 |
| Sample 5 | 68 |

Having thus described the invention in rather full detail, it will be readily apparent to a person having ordinary skill in the art that various changes and modifications can be made without departing from the spirit of the invention. All of such changes and modifications are contemplated as being within the scope of the invention, as defined by the subjoined claims.

We claim:

1. An absorbent article, comprising:
   a. a substantially liquid impermeable backsheet layer which delimits at least one waistband portion of said article;
   b. a substantially liquid permeable topsheet layer which is located in facing relation with an inner surface of said backsheet layer;
   c. an absorbent body located between said topsheet layer and said backsheet layer; and
   d. an elastic member connected to a selected surface of said waistband portion, said elastic member comprising an elastomeric nonwoven fibrous web material which is arranged to shirr said waistband portion and is composed of at least one layer of nonwoven fabric secured to a meltblown fibrous elastic layer, said elastic member having an untensioned bulk thickness of at least about 0.025 in, wherein said backsheet layer, topsheet layer and elastic member provide a composite waistband which has an untensioned total bulk thickness of at least about 0.050 in, has a buckling force value within the range of about 30–50 grams-force, and has a porosity value of at least about 3 cfm/sq. ft.

2. An absorbent article as recited in claim 1, wherein said backsheet layer is composed of a substantially vapor permeable polymer film.

3. An absorbent article as recited in claim 1, wherein said backsheet layer is composed of a substantially vapor permeable polymer film.

4. An absorbent article as recited in claim 1, wherein said elastic member is secured between said backsheet and topsheet layers.

5. An absorbent article as recited in claim 1, wherein said elastic member is secured to an outer surface of said backsheet layer.

6. An absorbent article as recited in claim 1, wherein said laminated composite waistband has a buckling force value within the range of about 35–45 grams-force.

7. An absorbent article as recited in claim 1, wherein said elastic element has a bulk thickness of at least about 0.05 in.

8. An absorbent article as recited in claim 7, wherein said composite waistband has a total bulk thickness of at least about 0.075 in.

9. An absorbent article as recited in claim 1, wherein said elastic member extends across at least about 40% of the cross-directional width of said article, and wherein said elastic member covers an area within the range of about 25–80 sq. cm.

10. An absorbent article, comprising:
    a. a backsheet layer delimiting at least one backsheet waistband portion, said waistband portion having a reduced-stiffness section therein;
    b. a substantially liquid permeable topsheet layer which is located in facing relation with an inner surface of said backsheet layer and spans at least partially over said reduced-stiffness section of said backsheet waistband portion;
    c. an absorbent body located between said topsheet layer and said backsheet layer; and
    d. a vapor-permeable elastic member connected to a surface of said backsheet waistband portion and spanning at least partially over the reduced-stiffness section thereof, wherein said elastic member has an untensioned bulk thickness of at least about 0.025 in and is composed of an elastomeric, nonwoven fibrous material arranged to shirr at least the part of said topsheet layer which spans over said reduced-stiffness section of said backsheet, and wherein said elastic member and topsheet layer comprise a composite waistband portion having a porosity value of at least about 3 cfm/sq. ft. and a bulking force value within the range of about 30–50 grams-force.

11. An absorbent article as recited in claim 10, wherein
    said backsheet layer has a front waistband portion and a back waistband portion;
    each of said front and back waistband portions has a reduced-stiffness section therein;
    a front elastic member, which is connected to an outer surface of said backsheet layer, spans completely over the reduced-stiffness section of the front waistband portion and is constructed and arranged to shirr at least a front portion of said topsheet layer; and
    a rear elastic member, which is connected to an outer surface of said backsheet layer, spans completely over the reduced-stiffness section of the rear waistband portion and is constructed and arranged to shirr at least a rear portion of said topsheet layer.

12. An absorbent article as recited in claim 10, wherein said reduced-stiffness section of said backsheet waistband is located at a medial position thereof.

13. An absorbent article as recited in claim 10, wherein said waistband reduced-stiffness section comprises at least one notched recess formed into a terminal edge of said waistband.

14. An absorbent article as recited in claim 10, wherein said waistband reduced-stiffness section comprises a plurality of apertures formed through said waistband.

15. An absorbent article as recited in claim 10, wherein said waistband reduced-stiffness section comprises a pattern of embossments formed into said waistband.

16. An absorbent article as recited in claim 10, wherein said composite waistband portion has a porosity value of at least about 5 cfm/sq. ft.

17. An absorbent article as recited in claim 16, wherein said composite waistband portion has a porosity value of at least about 10 cfm/sq. ft.

18. An absorbent article as recited in claim 10, further comprising a flow barrier for reducing the migration of liquids past said waistband portion.

19. An absorbent article as recited in claim 10, wherein said flow barrier comprises a flap, which is formed from said backsheet layer and folded over to overlap onto a bodyside of said absorbent body.

20. An absorbent article as recited in claim 10, wherein said elastic member comprises at least one layer of nonwoven fabric secured to a meltblown, fibrous elastic layer.

21. An absorbent article as recited in claim 10, wherein said composite waistband region has a buckling force value within the range of about 35–45 grams-force.

22. An absorbent article, comprising:
   a. a backsheet layer composed of a synthetic polymer film material and delimiting at least one backsheet waistband portion, said waistband portion having a reduced-stiffness section therein;
   b. a substantially liquid permeable topsheet layer which is located in facing relation with an inner surface of said backsheet layer and spans at least partially over the reduced-stiffness section of said waistband portion;
   c. an absorbent body located between said backsheet layer and said topsheet layer; and
   d. an elastic member connected to a surface of said backsheet layer and spanning at least partially over the reduced-stiffness secton of said backsheet waistband portion, wherein said elastic member has an untensioned bulk-thickness of at least about 0.025 in and is composed of an elastomeric, vapor-permeable, nonwoven fibrous material which is connected and arranged to shirr at least a waistband portion of said topsheet layer, and wherein said elastic member extends across at least about 40% of the cross-directional width of said article and covers an area within the range of about 25–80 sq. cm, said elastic member and topsheet layer comprising a composite waistband region which has a buckling force value within the range of about 30–50 grams-force and a porosity of at least about 3 cfm/sq. ft.

23. An absorbent article as recited in claim 22, wherein
   said backsheet layer has a front waistband portion and a back waistband portion;
   each of said front and back waistband portions has a reduced-stiffness section therein;
   a front elastic member, which is connected to an outer surface of said backsheet layer, spans completely over the reduced-stiffness section of the front waistband portion and is constructed and arranged to shirr at least a front portion of said topsheet layer; and
   a rear elastic member, which is connected to an outer surface of said backsheet layer, spans completely over the reduced-stiffness section of the rear waistband portion and is constructed and arranged to shirr at least a rear portion of said topsheet layer.

24. An absorbent article as recited in claim 22, wherein said reduced-stiffness section of said backsheet waistband is located at a medial position thereof.

25. An absorbent article as recited in claim 22, wherein said waistband reduced-stiffness section comprises at least one notched recess formed into a terminal edge of said waistband.

26. An absorbent article as recited in claim 22, wherein said waistband reduced-stiffness section comprises a plurality of apertures formed through said waistband.

27. An absorbent article as recited in claim 22, wherein said waistband reduced-stiffness section comprises a pattern of embossments formed into said waistband.

28. An absorbent article as recited in claim 22, wherein said composite waistband region has a porosity value of at least about 5 cfm/sq. ft.

29. An absorbent article as recited in claim 22, wherein said composite waistband region has a porosity value of at least about 10 cfm/sq. ft.

30. An absorbent article as recited in claim 22, further comprising a flow barrier for reducing the migration of liquids past said waistband portion.

31. An absorbent article as recited in claim 22, wherein said flow barrier comprises a flap, which is formed from said backsheet layer and folded over to overlap onto a bodyside of said absorbent body.

32. An absorbent article as recited in claim 22, wherein said elastic member comprises at least one layer of nonwoven fabric secured to a meltblown, fibrous elastic layer.

33. An absorbent article, comprising:
   a substantially liquid impermeable and substantially inelastic backsheet layer which delimits at least one backsheet waistband portion;
   a substantially liquid permeable topsheet layer which is located in facing relation with an inner surface of said backsheet layer;
   an absorbent body located between said topsheet layer and said backsheet layer; and
   an elastic member laminated between said backsheet and topsheet layers to form a gathered, composite waistband portion, wherein said elastic member is composed of an elastomeric nonwoven fibrous material having a thickness in its untensioned, contracted state of at least about 0.025 inch, and wherein said composite waistband portion has a buckling force value within the range of about 30–50 grams-force and a porosity value of at least about 3 cfm/sq. ft.

34. An absorbent article as recited in claim 33, wherein said elastic member is composed of an elastomeric, meltblown fibrous web.

35. An absorbent article as recited in claim 33, wherein said elastic member is composed of an elastomeric, stretch-bonded laminate web.

36. An absorbent article as recited in claim 33, wherein said elastic member has a thickness of at least about 0.050 inch.

37. An absorbent article as recited in claim 33, wherein said composite waistband portion has a buckling force value within the range of about 35–45 grams-force.

38. An absorbent article as recited in claim 33, further comprising a flow barrier for reducing the migration of liquids past said waistband portion.

39. An absorbent article as recited in claim 33, wherein said flow barrier comprises a flap, which is formed from said backsheet layer and folded over to overlap onto a bodyside of said absorbent body.

* * * * *